US011643445B2

(12) United States Patent
Millqvist Fureby et al.

(10) Patent No.: US 11,643,445 B2
(45) Date of Patent: May 9, 2023

(54) POROUS PROTEIN PARTICLES AS CARRIERS FOR ACTIVES

(71) Applicants: COLGATE-PALMOLIVE COMPANY, New York, NY (US); MONDELEZ GLOBAL LLC, East Hanover, NJ (US)

(72) Inventors: Anna Millqvist Fureby, Huddinge (SE); Amjad Farooq, Hillsborough, NJ (US); Claudio Ortiz, Dayton, NJ (US); Ammanuel Mehreteab, Yardley, PA (US); Gail Klewsaat, Neshanic Station, NJ (US); Mary Holmgren, Somerville, NJ (US); Yelloji-Rao Mirajkar, Piscataway, NJ (US); Jose Javier Tovar Pescador, Mexico City (MX); Oscar Bautista Cid, Mexico City (MX); Terrell Partee, Piscataway, NJ (US)

(73) Assignees: Colgate-Palmolive Company, New York, NY (US); Intercontinental Great Brands LLC, East Hanover, NJ (US)

( * ) Notice: Subject to any disclaimer, the term of this patent is extended or adjusted under 35 U.S.C. 154(b) by 247 days.

(21) Appl. No.: 15/569,073

(22) PCT Filed: Apr. 19, 2016

(86) PCT No.: PCT/US2016/028315
§ 371 (c)(1),
(2) Date: Oct. 24, 2017

(87) PCT Pub. No.: WO2016/172123
PCT Pub. Date: Oct. 27, 2016

(65) Prior Publication Data
US 2018/0134757 A1    May 17, 2018

Related U.S. Application Data

(60) Provisional application No. 62/152,635, filed on Apr. 24, 2015.

(51) Int. Cl.
*C07K 14/47*    (2006.01)
*A61Q 15/00*    (2006.01)
(Continued)

(52) U.S. Cl.
CPC ............. *C07K 14/47* (2013.01); *A23G 4/06* (2013.01); *A23G 4/08* (2013.01); *A23G 4/14* (2013.01); *A23J 3/08* (2013.01); *A23J 3/10* (2013.01); *A23J 3/16* (2013.01); *A23L 27/70* (2016.08); *A23L 29/262* (2016.08); *A23L 29/281* (2016.08); *A61K 8/0279* (2013.01); *A61K 8/06* (2013.01); *A61K 8/21* (2013.01); *A61K 8/25* (2013.01); *A61K 8/26* (2013.01); *A61K 8/27* (2013.01); *A61K 8/28* (2013.01); *A61K 8/29* (2013.01); *A61K 8/345* (2013.01); *A61K 8/368* (2013.01); *A61K 8/44* (2013.01); *A61K 8/442* (2013.01); *A61K 8/463* (2013.01); *A61K 8/49* (2013.01); *A61K 8/585* (2013.01);
(Continued)

(58) Field of Classification Search
CPC .... A23G 4/06; A23G 4/08; A23G 4/14; A23J 3/08; A23J 3/10; A23J 3/16; A23L 27/70; A23L 29/262; A23L 29/281; A23V 2002/00; A23V 2200/15; A23V 2250/18; A23V 2250/54252; A61K 8/06; A61K 8/21; A61K 8/25; A61K 8/26; A61K 8/27; A61K 8/28; A61K 8/29; A61K 8/44; A61K 8/49; A61K 8/64; A61K 8/86; A61K 8/345; A61K 8/368; A61K 8/442; A61K 8/463; A61K 8/585; A61K 8/645; A61K 8/731; A61K 8/0279; A61K 8/9794; A61K 8/9789; A61K 2800/28; A61K 2800/48; A61Q 11/00; A61Q 15/00; A61Q 19/00; C07K 14/47; C11B 9/00; C11D 3/38609; C11D 3/505
See application file for complete search history.

(56) References Cited

U.S. PATENT DOCUMENTS

| 4,089,848 A | * | 5/1978 | Bell ........................ A23J 1/12 |
| | | | 127/29 |
| 4,208,260 A | * | 6/1980 | Oughton ................. A23J 1/006 |
| | | | 204/560 |

(Continued)

FOREIGN PATENT DOCUMENTS

| CN | 102552174 | 7/2012 |
| WO | WO 2000/035295 | 6/2000 |

(Continued)

OTHER PUBLICATIONS

Singh et al.: A comparative study on chemical composition, color, and functional Characteristics of flours and protein concentrates from different Oat cultivars, International Journal of Recent Scientific Research, vol. 9, Issue, 5(C), pp. 2666-26671, May 2018 https://recentscientific.com/sites/default/files/109.*
International Search Report for International Application No. PCT/US2016/028315, dated Jul. 26, 2016, 3 pages.
Caric, M., et al., "Effects of Drying Techniques on Milk Powders Quality and Microstructure: A Review," Food Structure, 6(2): 171-180 (1987).
Alnaief et al., "In situ production of spherical aerogel microparticles" Journal of Supercritical Fluids; 55(2011) 1118-1123.
CN 102552174—Abstract of citation in English.

(Continued)

*Primary Examiner* — Hong Yu
(74) *Attorney, Agent, or Firm* — Hoxie & Associates LLC

(57) ABSTRACT

Disclosed are high-porosity protein particles useful for carrying one or more agents of interest, methods for their manufacture and use, and products comprising them.

16 Claims, No Drawings

(51) Int. Cl.

| | | |
|---|---|---|
| *A61K 8/64* | (2006.01) | |
| *A61K 8/9794* | (2017.01) | |
| *A61K 8/368* | (2006.01) | |
| *A61K 8/44* | (2006.01) | |
| *A61K 8/28* | (2006.01) | |
| *A61K 8/26* | (2006.01) | |
| *A61K 8/58* | (2006.01) | |
| *A61K 8/86* | (2006.01) | |
| *A61K 8/9789* | (2017.01) | |
| *A61Q 11/00* | (2006.01) | |
| *A61K 8/73* | (2006.01) | |
| *A61K 8/49* | (2006.01) | |
| *A61K 8/21* | (2006.01) | |
| *A61K 8/29* | (2006.01) | |
| *A61K 8/34* | (2006.01) | |
| *A61K 8/25* | (2006.01) | |
| *A61K 8/46* | (2006.01) | |
| *A61K 8/27* | (2006.01) | |
| *C11B 9/00* | (2006.01) | |
| *A23G 4/08* | (2006.01) | |
| *A23G 4/14* | (2006.01) | |
| *C11D 3/386* | (2006.01) | |
| *A23L 29/262* | (2016.01) | |
| *A23L 27/00* | (2016.01) | |
| *C11D 3/50* | (2006.01) | |
| *A23G 4/06* | (2006.01) | |
| *A23L 29/281* | (2016.01) | |
| *A61Q 19/00* | (2006.01) | |
| *A61K 8/06* | (2006.01) | |
| *A61K 8/02* | (2006.01) | |
| *A23J 3/10* | (2006.01) | |
| *A23J 3/08* | (2006.01) | |
| *A23J 3/16* | (2006.01) | |

(52) U.S. Cl.
CPC ............... *A61K 8/64* (2013.01); *A61K 8/645* (2013.01); *A61K 8/731* (2013.01); *A61K 8/645* (2013.01); *A61K 8/86* (2013.01); *A61K 8/9789* (2017.08); *A61K 8/9794* (2017.08); *A61Q 11/00* (2013.01); *A61Q 15/00* (2013.01); *A61Q 19/00* (2013.01); *C11B 9/00* (2013.01); *C11D 3/38609* (2013.01); *C11D 3/505* (2013.01); *A23V 2002/00* (2013.01); *A61K 2800/28* (2013.01); *A61K 2800/48* (2013.01)

(56) References Cited

U.S. PATENT DOCUMENTS

| | | | |
|---|---|---|---|
| 5,023,080 A * | 6/1991 | Gupta | ............... A01N 25/10 |
| | | | 424/405 |
| 5,079,005 A | 1/1992 | Gupta | |
| 5,601,760 A | 2/1997 | Rosenberg | |
| 6,132,750 A | 10/2000 | Perrier et al. | |
| 6,986,907 B2 | 1/2006 | Phillips et al. | |
| 7,888,410 B2 | 2/2011 | Nair et al. | |
| 7,998,477 B2 | 8/2011 | Yakovlevsky et al. | |
| 9,238,009 B2 | 1/2016 | Dollat et al. | |
| 2006/0040033 A1* | 2/2006 | Zeller | ............... A23C 11/08 |
| | | | 426/564 |
| 2008/0044551 A1 | 2/2008 | Subramaniam | |
| 2010/0267108 A1 | 10/2010 | Jordaan et al. | |

FOREIGN PATENT DOCUMENTS

| | | |
|---|---|---|
| WO | WO 2014/090920 | 6/2014 |
| WO | WO 2016/172123 | 10/2016 |

OTHER PUBLICATIONS

Chen et al., "Research Progress in Preparation of Porous Microspheres by Supercritical Carbon Dioxide Fluid Technology," Journals of Science, vol. 57, No. 36, pp. 3459-3466, (2012) (English translation).

* cited by examiner

POROUS PROTEIN PARTICLES AS CARRIERS FOR ACTIVES

CROSS REFERENCE TO RELATED APPLICATIONS

This application is a United States Application under 35 U.S.C. 371 claiming the benefit of International PCT Application No. PCT/US2016/028315, filed Apr. 19, 2016, which claims priority to U.S. Provisional Application No. 62/152,635, filed Apr. 24, 2015, the contents of each of which are incorporated herein by reference in their entirety.

BACKGROUND

A multitude of encapsulation technologies are known for controlled release of active ingredients in a variety of applications including adhesives, textiles, flavors, fragrances and pesticides. For example, mesoporous silica has been used as a carrier for active ingredients in several applications including catalysis, drug delivery and imaging, and mesoporous protein particles have been prepared by colloidal $CaCO_3$ templating and through templating mesoporous silica spheres.

Antiperspirants and deodorants are available in many forms, including for example sticks, emulsions, and aerosol sprays, which typically contain fragrance in addition to a carrier material and optionally an antiperspirant compound. One significant challenge in formulating an antiperspirant or deodorant product is to achieve continuous release of fragrance and/or other actives from the composition for a significant time after application.

Scent boosters are products that contain fragrance-containing solids, usually along with detergent. The fragrance-containing solids provide enhanced fragrance perception at the end of washing, as well as in the dried garment, when tumble dried at elevated temperatures. One consideration in the design of scent boosters for use in wash or rinse cycles is that the fragrance is effectively imparted to the garments, and is not washed away.

There is an ongoing need for new encapsulation technologies that utilize nontoxic materials, such as fragrances, food substances, scent boosters, flavors, antibacterials and other actives, and that have controlled pore size and are suitable for carrying the actives for applications in the food, personal care and other industries that involve exposure to humans and animals.

BRIEF SUMMARY

In some embodiments, the present disclosure provides porous protein particles that contain one or more agents of interest loaded therein, and compositions comprising the particles.

In some embodiments, the present disclosure provides methods for preparing porous protein particles, comprising providing a protein isolate such for example as native or denatured whey protein isolate; forming a protein isolate stabilized emulsion comprising the protein isolate and an oil in an aqueous media; drying the emulsion to produce a powder; and extracting oil from the powder to produce the porous protein particles; as well as particles made thereby.

In some embodiments, the forming of the protein isolate stabilized emulsion is performed by mixing, homogenizing or fluidizing the protein isolate together with an oil optionally in the presence of one or more additives that can include surfactants and/or modified celluloses. The emulsion can then be dried, and the oil extracted with a solvent that can be an organic solvent, or a supercritical fluid, for example supercritical carbon dioxide, to yield porous protein particles with defined properties.

The particles thus formed are highly porous and, being made of protein, may be loaded with hydrophilic and/or lipophilic agents of interest, which will fill the pores of the protein particle. If the protein particle loaded with an agent of interest (e.g., flavoring, fragrance or active agent) and the loaded particle is then incorporated into a formulation, the particle may delay the release of the agent of interest until the particle breaks or disintegrates during or after use of the formulation, thereby providing a sustained fragrance, taste or release of active agent, as the case may be. The particles moreover may isolate and protect the agent of interest from interaction with other formulation components prior to use, thereby facilitating incorporation of the agent of interest into the formulation and reducing interaction of the agent of interest with other formulation excipients. The particles thus may be used for the delivery of agents of interest, for example flavors, e.g., in confectionary or food products (for human or animal use), or in toothpaste; or fragrances, e.g., in underarm products, body washes or fabric care products; or active ingredients for oral care, e.g. in toothpaste; or for delivery of vitamins or other active agents.

The present disclosure thus provides protein particles, e.g., made as described above, and further comprising hydrophilic and/or lipophilic agents of interest (e.g., flavorings, fragrances and/or active agents) incorporated therein, as well as formulations comprising such particles, e.g., home care, personal care, oral care, food or confectionary products.

In some embodiments, the present disclosure provides antiperspirant or deodorant compositions comprising at least one of an antiperspirant active, a deodorant active, and free fragrance, and a plurality of protein particles containing a fragrance, and methods for their use. In some embodiments, the protein comprises denatured whey protein, or an isolate thereof.

In some embodiments, the present disclosure provides a body wash or other personal care product comprising a plurality of protein particles containing a fragrance, and methods for their use. In some embodiments, the protein comprises denatured whey protein, or an isolate thereof.

In some embodiments, the present disclosure provides a laundry additive composition comprising (i) porous protein particle comprising a fragrance agent of interest loaded therein, and (ii) one of a water soluble carrier or a dryer sheet. In some embodiments, the water soluble carrier is at least one of an oxylated material and a salt. In further embodiments, the oxylated material is at least one material chosen from polyoxyalkylene, a polyoxyalkylene fatty acid ester, and a polyoxyalkylene fatty alcohol ether. In further embodiments, the salt is at least one of sodium sulfate and sodium carbonate. In some further embodiments, the composition further comprises at least one fabric conditioning material chosen from a fabric softener or a silicone.

In some embodiments, the disclosure provides a confectionary product, for example a chewing gum or hard candy, comprising a plurality of protein particles containing a flavor, for example a lipophilic flavoring, for example a flavoring oil or extract or combination of flavoring oils and/or extracts, and/or containing a sweetening agent; and methods for their use. In some embodiments, the protein comprises denatured whey protein, or an isolate thereof.

In some embodiments, the disclosure provides a pet chew or other pet food product, e.g., for a dog, comprising a plurality of protein particles containing a flavor, for example a lipophilic flavoring, for example a flavoring oil or extract or combination of flavoring oils and/or extracts, and methods for their use. In some embodiments, the protein comprises denatured whey protein, or an isolate thereof.

In some embodiments, the disclosure provides an oral care product, for example a toothpaste, comprising a plurality of protein particles containing an agent of interest, for example a lipophilic agent, for example a flavoring agent and/or an active agent, for example a herbal extract or oil having antibacterial and/or flavoring properties. In some embodiments, the protein comprises denatured whey protein, or an isolate thereof.

Further areas of applicability of the present disclosure will become apparent from the detailed description provided hereinafter. It should be understood that the detailed description and specific examples, while indicating the preferred embodiment of the disclosure, are intended for purposes of illustration only and are not intended to limit the scope of the disclosure.

DETAILED DESCRIPTION

The following description of the preferred embodiment(s) is merely exemplary in nature and is in no way intended to limit the disclosure, its application, or uses.

As used throughout, ranges are used as shorthand for describing each and every value that is within the range. Any value within the range can be selected as the terminus of the range. In addition, all references cited herein are hereby incorporated by referenced in their entireties. In the event of a conflict in a definition in the present disclosure and that of a cited reference, the present disclosure controls.

Unless otherwise specified, all percentages and amounts expressed herein and elsewhere in the specification should be understood to refer to percentages by weight. The amounts given are based on the active weight of the material.

Particle Manufacture

It has been discovered in accordance with the present disclosure that porous particles can be generated by using an emulsion templating method wherein a proteinaceous matrix material is emulsified with an oil-based templating material, optionally in the presence of a surfactant, and the emulsion is dried and the oil phase extracted using solvent, for example an organic solvent, or supercritical carbon dioxide ($SCCO_2$). The particles thus produced can be carriers for a variety of active agents, for example food substances, food acids, starches, carbohydrates, beverages, pharmaceuticals, biocides, pesticides, benefit agents and personal care products, including but not limited to anhydrous products such as antiperspirant sticks and aerosols, and for example, scent booster compositions.

In some embodiments the disclosure provides methods for preparing a porous protein particle, comprising: providing a protein isolate; emulsifying an oil with one or more surfactants to produce an emulsion also containing the protein isolate; drying the emulsion to produce a powder; and extracting the powder to produce the porous protein particle. In further embodiments, the disclosure provides methods of loading one or more active agents into the porous protein particles, and porous protein particles having at least one active agent loaded therein.

A variety of protein isolates can be used in accordance with the methods of the disclosure. In general, preferred protein isolates are nontoxic and preferably suitable for use in foods and supplements. In some embodiments, the protein isolates can be from a dairy protein, for example a milk protein fraction. One preferred protein isolate is whey protein isolate, such as, for example and not limited to, whey protein isolate sold by Arla Foods Ingredients under the name Lacprodan, for example Lacprodan DI9224. Whey protein isolates from other sources like Davisco (Bipro with >92% protein content on dry basis and highly functional) or Hilmar Ingredients (89% and higher in purity, native/highly functional and instantized for easy dispersion) are all suitable for making protein particles. Other suitable proteins and protein isolates include casein, sodium caseinate, soy protein isolate (Supro EX 38 and others with higher than 89% protein content), egg white proteins, ovalbumin, non allergenic rice protein isolate (Remypro 80 from Orafti), potato protein isolates (Solanic from Avebe), Canola protein isolates (Bio Exx), pea protein isolates (Pisane from A&B Ingredients, Nutralys from Roquette), and bovine serum albumin.

In some embodiments, the protein isolate, for example whey protein isolate (WPI), is denatured prior to emulsification in accordance with the methods of the disclosure. Denaturation can be achieved by, for example, heating an aqueous solution or suspension of the protein isolate, for example to 75° C., or 80° C., or higher for 10 minutes, 20 minutes or longer. The denaturation renders the final protein particles insoluble in water.

The protein isolate is typically emulsified with an oil to produce an emulsion. The emulsion is then dried, and extracted to remove the oil. While not wishing to be bound by any particular theory, it is believed that in general, the denatured or native protein or protein isolate, for example whey protein isolate or denatured whey protein isolate, functions as the matrix material and emulsifier, while the oil, for example triglyceride oils, function as the templating lipid. Additional additives, including modified celluloses such as hydroxypropylmethylcellulose (HPMC) and methylcellulose (MeC), and surfactants such as polysorbates (for example Tween™ 80 or Tween™ 60) and lecithin can be used as emulsifiers, and are thought to enhance the extraction efficiency when removing the oil template by extraction using different solvents, for example and not limited to acetone and petroleum ether. As used throughout, modified cellulose refers to one or more of alkyl celluloses, hydroxyalkyl celluloses, and hydroxyalkyl alkyl celluloses.

The emulsification of oil and creation of a protein containing emulsion can be performed in accordance with any of several procedures. For example, in some embodiments, the triglyceride oil is emulsified by mixing the oil with a solution of native or heat-denatured whey protein isolate, and passing the pre-emulsion through a high-pressure homogenizer to obtain an emulsion. Preferably, the emulsion has an average droplet size of 100-200 nm. Then, optionally, a modified cellulose such as hydroxypropylmethylcellulose (HPMC) or methylcellulose (MeC) is added, and the emulsion is dried, for example by spray drying. Alternatively, the oil is emulsified using a surfactant, which can be a non-ionic surfactant such as a polysorbate, for example Tween™, preferably Tween 80™, an amphipathic surfactant such a lipid surfactant, for example lecithin, or a modified cellulose. The emulsion is passed through the high-pressure homogenizer, and then mixed with heat denatured whey protein solution.

In some embodiments, formation of the protein isolate emulsion is achieved by preparing a mixture comprising an oil, a surfactant, and water; homogenizing or fluidizing the mixture to form a surfactant stabilized emulsion; combining the protein isolate in solution and the surfactant stabilized emulsion to form a protein isolate-surfactant stabilized emulsion; and optionally combining the protein isolate-surfactant stabilized emulsion with a further component, for example a surfactant, for example a modified cellulose such as MeC.

In some further embodiments, formation of the protein isolate emulsion is achieved by preparing a mixture comprising the protein isolate, a modified cellulose polymer (for example MeC or HPMC) and water, and the mixture is then combined with an oil as described above to form an emulsion, which is then homogenized or fluidized as described above.

In some further embodiments, formation of the protein isolate emulsion is achieved by mixing surfactant, preferably a nonionic surfactant, for example a polysorbate such as Tween™ 80, with the native or denatured protein isolate to form an aqueous solution, and the oil is added to the surfactant-protein isolate solution, and is mixed and homogenized or fluidized as described above.

In some further embodiments, emulsification is achieved by mixing amphipathic surfactant, for example lecithin, with the oil to form a solution and adding this solution to water to form an emulsion, and homogenizing or fluidizing the emulsion as described above. The resulting emulsion is then combined with the native or denatured protein isolate in solution.

It has been surprisingly found that when $SCCO_2$ is used as the extraction solvent, it is unnecessary to include either surfactant or modified cellulose in the emulsion. Thus, in some embodiments, the particles of the disclosure can be prepared by combining the oil with the protein isolate in water solution; and homogenizing or fluidizing the mixture to form an emulsion. The resulting emulsion is dried and then extracted with a supercritical fluid, for example $SCCO_2$.

A variety of oils can be used in the present disclosure. Suitable oils include triglyceride oils, in particular vegetable oils. Preferred oils include, without limitation, rapeseed oil, soybean oil, and triglyceride oils, for example medium-chain triglyceride oil, which are available from, for example, AarhusKarlshams (Aarhus, Denmark), as well as sunflower oil, and other liquid vegetable oils. As used throughout, medium-chain triglyceride oil refers to a triglyceride oil that has $C_6$ to $C_{12}$ fatty acids.

A variety of surfactant materials can be used in the methods of the present disclosure in addition to denatured whey protein isolate (dWPI), which itself acts as an emulsifier. Preferably surfactants used in accordance with the disclosure are nontoxic. Suitable surfactants include nonionic surfactants, amphipathic surfactants and modified celluloses such as MeC, HPMC and mixtures thereof.

Suitable nonionic surfactants include polyoxyethylene fatty acid esters (polysorbates), such as, for example, polysorbate 20, polysorbate 60, polysorbate 65, polysorbate 80, (sold under the name Tween™ 80), and the like.

Suitable amphipathic surfactants include lipids, and lipid mixtures such as lecithin, sucrose esters, polyglyceryl esters of high moderate to high HLB (8 to 18). Mixtures of surfactants can be also used such as Tweens in water phase (HLB 14 to 18) and Spans (sorbitan esters of low HLB (1 to 6, for example 1 to 3)) in oil phase to form very stable interfaces.

Further examples of suitable surfactants include the aforementioned modified celluloses. Preferably, the modified cellulose is hydroxypropyl methyl cellulose (HPMC), methyl cellulose (MeC) or hydroxypropyl cellulose. In some preferred embodiments, the HPMC has a 1.9 degree of substitution per monomer for Me groups and a 0.9 degree of substitution per monomer for hydroxypropyl groups. The MeC preferably has a degree of substitution of 1.5 to 1.9 (27.5-31.5% by weight).

In some embodiments, the oil and surfactant are mixed together with a solvent, which is preferably water. For example, in some embodiments, the oil is added to a solution of the surfactant dissolved in water. The resulting mixture of oil, surfactant, and solvent can then be homogenized and then combined with native or denatured protein isolate to form a protein isolate-surfactant stabilized emulsion. In some embodiments, a further emulsion is formed by addition of a further surfactant, which can be a surfactant as described above. In some such embodiments, the further surfactant is a modified cellulose, for example HPMC or MeC.

Typically, homogenization or fluidization is performed at high speed for a suitable period of time. Any conventional high speed mixing apparatus can be used, for example an UltraTurrax mixer at high speed (e.g., 24,000 rpm). Typically, the mixing is performed for a time sufficient to ensure complete mixing—for example from one to five minutes, for example two minutes. The resulting mixture is the typically passed through a microfluidizer at high pressure, for example at 650 bar, multiple times, for example from four to twenty times. In some embodiments, the emulsion is homogenized or fluidized to achieve an average droplet diameter of from 100 nm to 1000 nm, for example about 200 nm. The resulting emulsion can then be dried, and the oil extracted, as discussed below.

After the emulsion is formed, it is dried to produce a powder. One preferred technique for drying the emulsion is spray drying, in which the emulsion is rapidly dried with a hot gas, for example air or an inert gas such as nitrogen. Spray drying techniques are well known in the art. Other suitable drying techniques useful in the present disclosure include spray freezing and freeze drying. Typically, the dried particles are collected as a powder, and then the oil component is extracted.

Extraction of oil from the dried particles can be accomplished using a variety of organic solvents, or with supercritical fluids. Useful organic solvents include ethanol, petroleum ether, acetone, and low molecular weight (i.e., $C_4$-$C_8$) hydrocarbons. For extraction with organic solvents, samples are typically contacted with the solvent, for example in any convenient container, and the mixture is agitated, for example stirred or shaken for a suitable period of time, for example from one to about ten minutes, for example about two minutes. Solvent can then be separated by any convenient means, such as for example by filtration, and the particles collected and dried, for example in an oven, to remove trace solvent.

Extractions using supercritical fluids are performed above the critical temperature and pressure of the solvent. One preferred supercritical fluid for oil extraction is supercritical carbon dioxide ($SCCO_2$), which is known to have a critical temperature of 31° C. and a critical pressure of 74 bar. Thus, extraction with $SCCO_2$ is preferably performed at high pressure in excess of 74 bar, for example about 300-400 bar, for example about 350 bar, and at a temperature above 31° C., for example from about 35° C. to 50° C., for example about 45° C. The $SCCO_2$ can optionally contain one or more co-solvents. Examples of suitable co-solvents include methanol, ethanol and acetone. Extraction is typically carried out for a period of time sufficient to ensure removal of as much oil as possible, typically from about ten minutes to several hours, for example about one hour. Preferably, the oil is continuously removed throughout the extraction.

The particles produced by the methods of the disclosure can range in size from approximately 500 nm to 20 μm or larger. Larger particle sizes can be achieved by use of suitable spray-drying equipment, as in known in the art. Pore sizes in the particles can vary, typically from about 50-300 nm. The homogenization process should be vigorous to achieve the smaller pore sizes, for example by use of a microfluidizer.

In some embodiments, spray dried or freeze dried particles comprising native WPI can be heated at 60-85° C., with 30-80% RH (relative humidity) to manipulate surface and interior hydrophobicity of the particles.

The particles prepared by the processes of the disclosure are excellent carriers for a wide variety of agents of interest. Thus, the particles prepared by the processes of the disclosure can be loaded with one or more agents of interest. As used herein, the terms "load", "loaded", "loading", "carry" and "carrying" as used in regard to the protein particles described herein, mean that the particles have been contacted with the active in a manner sufficient to cause active to penetrate that particle pores, and/or adsorb to the particle surface, and thus allow the particle to function as a carrier for the active.

Suitable agents of interest ("actives") can include, for example, flavors, fragrances, nutrients, active substances, food substances, taste-masking substances, biocides, pesticides, vitamins, benefit agents and personal care substances.

In some embodiments, the extracted particles can be loaded with one or more actives, for example flavors, fragrances, nutrients, active substances, taste-masking substances, biocides, pesticides herbicides, vitamins, essential oils, water soluble and insoluble plant extracts, preservatives, antioxidants, food acids (including, e.g., citric acid, tartaric acid, malic acid, fumaric acid, and lactic acid), starches, carbohydrates, and personal care substances. The loaded particles carrying the active can then be included in a variety of products, for example beverages, pharmaceuticals, biocides, pesticides and personal care products, for example antiperspirants, deodorants, scent booster compositions, toothpastes, moisturizers and food substances.

In some embodiments, the active can be antiperspirant compounds, such as aluminum-containing salts and zirconium-containing salts or materials, such as, for example, aluminum halides, aluminum hydroxyhalides, zirconyl oxyhalides, zirconyl hydroxyhalides, for example, aluminum chloride, aluminum chlorohydrate, and aluminum-zirconium compounds such as aluminum zirconium tetrachlorohydrate gly and aluminum zirconium tetrachlorohydrex gly and mixtures thereof; for example any of the materials classified and approved for use as antiperspirants by the United States Food and Drug Administration under 21 CFR part 350; odor-reducing compounds, such as odor reducing agents such as a sulfur precipitating agent, e.g., copper gluconate, zinc gluconate, zinc citrate, and the like.

In some further embodiments, the active can be fragrances useful in laundry products, for example as carriers for fragrances in scent booster compositions.

In some embodiments, the particles of the present disclosure can be utilized as flavor carriers in a variety of food substances, including baked goods, candies, confections, and chewing gums. Porous protein particles according to the disclosure carrying flavor or other actives can be incorporated into the food during processing to provide a controlled release of flavor. Conditions such as pH and choice of protein (e.g., denatured or native whey protein) can be chosen to affect the release of the active form the particle, as discussed below. Thus, the particles disclosed herein can be used to effect rapid or more slow release of flavor, providing a sustained flavor or a flavor burst.

In some further embodiments, the active can be an antibacterial agent. Such antibacterial agents are routinely used in a variety of products retard bacterial growth in the product, and especially as a germicide, for example in oral care products such as toothpastes. Accordingly, the particles disclosed herein can be used as a carrier for antibacterial agents, and particularly such agents having a hydrophobic nature.

In some further embodiments, the active can be a food acid. Food acids are typically added to foods to make flavors "sharper", and also act as preservatives and antioxidants. Common food acids suitable as actives in the particles of the present disclosure include, e.g., citric acid, tartaric acid, malic acid, fumaric acid, and lactic acid.

Typically, the extracted particles are placed in a suitable container, and the active substance, optionally dissolved in non-aqueous solvent, is added slowly with agitation, for example stirring. Typically, active is added until either the powder just begins to become too cohesive, or when the predesired amount of active has been added. Typical loading levels are up to 50%. The loaded particles can then be dried by, for example, filtration and/or oven drying, and stored for later use. The loaded particles are then formulated into a desired composition, for example an antiperspirant or deodorant composition, or a laundry additive composition.

In some embodiments, extracted protein particles can be loaded in situ, during processing of a desired formulation. For example, extracted protein particles not containing active can be added to a desired formulation containing one or more agents of interest (e.g. a fragrance), and the protein particles can load with active during processing of the formulation.

In some embodiments, for example in some antiperspirant or deodorant compositions, the compositions can be anhydrous. By anhydrous it is meant that the composition does not contain more than 5 weight % free water not including any water of hydration. In other embodiments, anhydrous means less than 2 or less than 1 weight % free water.

The disclosure further provides any foregoing Composition, wherein the particle or particles in the composition comprise native whey protein isolate.

The disclosure further provides, in further embodiments, any preceding particle or composition, prepared by any of the preceding methods.

The disclosure further provides, in one embodiment, a food substance, beverage, pharmaceutical, biocide, pesticide or personal care product comprising a porous protein particle prepared by any foregoing method. The disclosure further provides the use of a porous protein particle prepared by any foregoing method in the manufacture of a food substance, beverage, pharmaceutical, biocide, pesticide or personal care product.

The disclosure provides, in one embodiment, a method (Method 1) for preparing a porous protein particle, comprising: providing a protein isolate; forming a protein isolate emulsion with an oil; drying the emulsion to produce a powder; and extracting the oil from the powder to produce the porous protein particle; for example:

1.1. Method 1, wherein the protein isolate emulsion is formed by a procedure comprising:
(i) emulsifying an oil with one or more surfactants with moderate to high HLB (8 to 18), for example the protein isolate, a polysorbate such as Tween, lecithin or a modified cellulose; or
(ii) emulsifying an oil with a high HLB (14 to 18) surfactant in the water phase and a low HLB (1 to 6, e.g., 1 to 3) surfactant in the oil phase; or
(iii) mixing a surfactant stabilized emulsion with the protein isolate.

1.2. Method 1 or 1.1, wherein the emulsifying of the protein isolate comprises any of procedures (a)-(e):
(a) i) providing a mixture comprising an oil, for example rapeseed oil, soybean oil, or a triglyceride oil such as a medium-chain triglyceride oil; a surfactant such as for example a nonionic detergent such as for example polysorbate surfactants such as Tween, amphipathic surfactants such as lecithin, or modified celluloses; and water;
ii) homogenizing or fluidizing the mixture to form a surfactant stabilized emulsion;
iii) combining the protein isolate and the surfactant stabilized emulsion to form a protein isolate-surfactant stabilized emulsion; and
iv) optionally combining the protein isolate-surfactant stabilized emulsion with a further component, for example a surfactant, for example a polymeric surfactant, for example a modified cellulose;
(b) i) providing a mixture comprising the protein isolate, a modified cellulose surfactant (for example MeC or HPMC), and water;
ii) combining the mixture with an oil, for example a triglyceride oil, to form an emulsion; and
iii) homogenizing or fluidizing the emulsion;
(c) i) providing a mixture comprising the protein isolate and a surfactant (for example a polysorbate such as Tween);
ii) combining the mixture with an oil, for example a triglyceride oil, to form an emulsion; and
iii) homogenizing or fluidizing the emulsion;
(d) i) providing a mixture comprising an oil, for example a triglyceride oil, an amphipathic surfactant, for example lecithin, and water to form an emulsion;
ii) homogenizing or fluidizing the emulsion;
iii) combining the protein isolate and the emulsion;
(e) i) combining an oil, for example a triglyceride oil, with the protein isolate and water; and
ii) homogenizing or fluidizing the mixture to form an emulsion.

1.3. Any foregoing method, wherein the protein isolate is dissolved or suspended in water.
1.4. Any foregoing method, wherein the protein isolate is at least one protein isolate chosen from whey protein isolate, soy protein isolate, casein, sodium caseinate, egg white proteins, ovalbumin, rice protein isolate, potato protein isolates, canola protein isolates, pea protein isolates and bovine serum albumin; each of which can be either native or denatured.
1.5. The method of Method 1.4, wherein the protein isolate is whey protein isolate (WPI).
1.6. The method of Method 1.4, wherein the protein isolate solution is heat treated to form denatured whey protein isolate (dWPI).
1.7. The method of Method 1.4, wherein the protein isolate is soy protein isolate.
1.8. Any foregoing method, wherein the oil is selected from rapeseed oil, soybean oil, and medium-chain triglyceride oil.
1.9. Any foregoing method, wherein the drying process is spray drying.
1.10. Any foregoing method, wherein the drying is spray drying and freeze drying.
1.11. The method of any of Methods 1.2 to 1.10, wherein the modified cellulose comprises one or more of hydroxypropyl methyl cellulose (HPMC), methyl cellulose (MeC) and hydroxypropyl cellulose.
1.12. The method of any of Methods 1.2 to 1.10, wherein the modified cellulose comprises methyl cellulose.
1.13. Any foregoing method, wherein the extracting of the powder comprises extracting with supercritical carbon dioxide.
1.14. Any foregoing method, wherein the extracting of the powder comprises extracting with an organic solvent.
1.15. The method of Method 1.14, wherein the organic solvent comprises one or more of acetone, ethanol, and petroleum ether.
1.16. Any foregoing method, wherein the emulsion is homogenized to produce an average droplet diameter of from 100 nm to 1000 nm.
1.17. The method of Method 1.16, wherein the average droplet diameter is 100 nm to 300 nm, or about 200 nm.
1.18. Any foregoing method, wherein the protein is denatured whey protein isolate (dWPI); the surfactant is selected from nonionic surfactants, amphipathic surfactants, lecithin and modified celluloses; the oil is selected from rapeseed oil, soybean oil, triglyceride oils and medium-chain triglyceride oil; the drying is spray drying; the solvent is water; and the modified cellulose comprises one or more of hydroxypropyl methyl cellulose (HPMC), methyl cellulose (MeC) and hydroxypropyl cellulose.
1.19. The method of Method 1.18, wherein the surfactant is selected from polysorbates (for example a Tween polysorbate), lecithin, polyglyceryl esters, sucrose esters, sorbitan esters, and modified celluloses; the oil is selected from rapeseed oil and medium-chain triglyceride oil; the drying is spray drying and freeze drying; the modified cellulose comprises methyl cellulose (MeC); and the extracting of the powder comprises extracting with supercritical carbon dioxide.
1.20. Any of methods 1.2-1.19, wherein the forming of the protein isolate emulsion comprises procedure (a).
1.21. Any of methods 1.2-1.19, wherein the forming of the protein isolate emulsion comprises procedure (b).
1.22. Any of methods 1.2-1.19, wherein the forming of the protein isolate emulsion comprises procedure (c).
1.23. Any of methods 1.2-1.19, wherein the forming of the protein isolate emulsion comprises procedure (d).
1.24. Any of methods 1.2-1.19, wherein the forming of the protein isolate emulsion comprises procedure (e); and wherein the extracting is performed using $SCCO_2$.
1.25. Any of methods 1.2-1.19, wherein the particles comprise native whey protein isolate; and the method further comprises the step of heating the powder at 60-85° C. at 30-80% relative humidity.
1.26. A porous protein particle prepared by any of the foregoing methods.

The disclosure further provides, in one embodiment, a method (Method 2) for loading one or more agents of interest into a porous protein particle, comprising contacting said agent of interest with a porous protein particle, e.g., prepared by a method of any of the Methods 1 et seq., for a time and under conditions effective to load said agent of interest; for example:

2.1 Method 2 further comprising a step of adjusting the pH of the protein particles.

2.2 Method 2 or 2.1, wherein each agent of interest is independently selected from flavorings, fragrances, nutrients, active substances, taste-masking substances, biocides, pesticides herbicides, vitamins, essential oils, water soluble and insoluble plant extracts, preservatives, antioxidants, food acids, starches, carbohydrates and personal care substances.

2.3 Method 2.2 wherein the active substance is a fragrance, a flavoring, an oral care active, an antiperspirant active, a deodorant active, a food acid, a starch or a carbohydrate.

The disclosure further provides, in a further embodiment, a Porous Protein Particle (Particle 1) having an average diameter of from 500 nm to 20 μm, for example:

1.1. Particle 1, wherein the protein is selected from one or more of whey protein isolate, soy protein isolate, casein, sodium caseinate, egg white proteins, ovalbumin, non allergenic rice protein isolate, potato protein isolates, canola protein isolates, pea protein isolates and bovine serum albumin; each of which can be either native or denatured.

1.2. Particle 1, wherein the protein is selected from whey protein isolate, denatured whey protein isolate, soy protein isolate and denatured soy protein isolate.

1.3. Any foregoing Particle 1 et seq., wherein the specific surface area of the particle is 3-16 $m^2/g$, for example 5-14 $m^2/g$, e.g., 7-12 $m^2/g$.

1.4. Any foregoing Particle 1 et seq., wherein the internal surface area of the particle is 20-80 $m^2/g$, for example 30-70 $m^2/g$, for example 40-60 $m^2/g$.

1.5. Any foregoing Particle 1 et seq., wherein the pore volume of the particles is 0.1-0.6 ml/g, for example 0.2-0.5 ml/g, for example 0.3-0.4 ml/g.

1.6. Any foregoing Particle 1 et seq., wherein the specific surface area of the particle is 3-16 $m^2/g$, the internal surface area of the particle is 20-80 $m^2/g$, and the pore volume of the particles is 0.1-0.6 ml/g.

1.7. Any foregoing Particle 1 et seq., wherein the specific surface area of the particle is 5-14 $m^2/g$, the internal surface area of the particle is 30-70 $m^2/g$, and the pore volume of the particles is 0.2-0.5 ml/g.

1.8. Any foregoing Particle 1 et seq., wherein the protein is native or denatured whey protein isolate.

1.9. Any foregoing Particle 1 et seq., wherein the particle has one or more characteristics selected from a specific surface area of 7-12 $m^2/g$; an internal surface area of 40-60 $m^2/g$; and a pore volume of 0.3-0.4 ml/g, e.g., wherein the Particle has all of these characteristics.

1.10. Any foregoing Particle 1 et seq., further comprising an agent of interest loaded therein, e.g., an agent of interest selected from flavorings, fragrances, nutrients, active substances, taste-masking substances, biocides, pesticides herbicides, vitamins, essential oils, water soluble and insoluble plant extracts, preservatives, antioxidants, food acids, starches, carbohydrates and personal care substances; for example wherein the active substance is a fragrance, a flavoring, an oral care active, an antiperspirant active, a deodorant active, a food acid, a starch or a carbohydrate.

1.11. Particle 1.8, wherein the agent of interest is a fragrance.

1.12. Particle 1.8 wherein the agent of interest is a flavoring.

1.13. Particle 1.8 wherein the agent of interest is a food acid, a starch or a carbohydrate.

In a further embodiment, the disclosure provides a Composition (Composition 1) comprising a porous protein particle in combination or association with a carrier, for example:

1.1. Composition 1, wherein the porous protein particle is a particle according to any of Particles 1 et seq. above.

1.2. Composition 1, or 1.1 wherein the specific surface area of the particles (excluding any agent of interest) is 3-16 $m^2/g$, for example 5-14 $m^2/g$, for example 7-12 $m^2/g$.

1.3. Any foregoing Composition, wherein the internal surface area of the particles is 20-80 $m^2/g$, for example 30-70 $m^2/g$, for example 40-60 $m^2/g$.

1.4. Any foregoing Composition, wherein the pore volume of the particles is 0.1-0.6 ml/g, for example 0.2-0.5 ml/g, for example 0.3-0.4 ml/g.

1.5. Any foregoing Composition, wherein the protein is native or denatured whey protein isolate.

1.6. Any foregoing Composition, comprising a plurality of the porous protein particles.

1.7. Any foregoing Composition, wherein the particles prepared by any of the preceding Methods 1 et seq. or 2 et seq.

1.8. Composition 1.7 wherein the particle or particles in the composition comprise native whey protein isolate; and the method further comprises the step of heating the powder at 60-85° C. at 30-80% relative humidity.

1.9. Any foregoing Composition, comprising a plurality of the porous protein particles according to any of Particles 1 et seq., wherein the particles have loaded therein at least one agent of interest, e.g., selected from flavors, fragrances, nutrients, active substances, taste-masking substances, biocides, pesticides, herbicides, vitamins, essential oils, water soluble and insoluble plant extracts, antioxidants, food acids, starches, carbohydrates and personal care substances.

1.10. Any foregoing Composition, e.g., wherein the loaded particles provide an effective amount of said agent of interest; e.g., wherein the particles are loaded with flavoring and are present in the Composition in a concentration effective to impart flavor, or wherein the particles are loaded with fragrance and are present in the Composition in a concentration effective to impart fragrance, or wherein the particles are loaded with an active agent and are present in the Composition in a concentration effective to impart the desired activity.

1.11. Any foregoing composition wherein the carrier is wherein the carrier is selected from carriers for personal care products, e.g., an antiperspirant, or deodorant; home care products, for example a fabric care product; oral care products, for example a toothpaste; food products; or confectionary products, for example a chewing gum or hard candy.

The disclosure further provides any foregoing Composition, wherein the particle or particles in the composition comprise native whey protein isolate.

The disclosure further provides, in further embodiments, any preceding particle or composition, prepared by any of the preceding methods.

The disclosure further provides, in one embodiment, a food substance, beverage, pharmaceutical, biocide, pesticide, oral care product, or personal care product comprising a porous protein particle prepared by any foregoing method.

The disclosure further provides the use of a porous protein particle prepared by any foregoing method in the manufacture of a food substance, beverage, pharmaceutical, biocide, pesticide or personal care product.

The porous protein particles loaded with active can be added directly during the manufacture of a composition as described herein, or may first be incorporated into a matrix, for example a starch or carbohydrate matrix, for convenient addition during manufacture of a composition as disclosed herein.

Personal Care Products Comprising the Particles

In some embodiments the disclosure provides an antiperspirant or deodorant composition comprising (i) at least one of an antiperspirant active, a deodorant active, and free fragrance, and (ii) a plurality of protein particles containing a fragrance. In some embodiments, the composition is anhydrous. By anhydrous it is meant that the composition does not contain more than 5 weight % free water not including any water of hydration. In other embodiments, anhydrous means less than 2 or less than 1 weight % free water.

The disclosure further provides, in one embodiment, an antiperspirant or deodorant composition (Composition 2) comprising (i) at least one of an antiperspirant active, a deodorant active, and free fragrance, and (ii) a plurality of protein particles containing a fragrance; for example:

2.1. Composition 2, wherein the protein is at least one protein chosen from whey protein isolate, soy protein isolate, casein, sodium caseinate, egg white protein, ovalbumin, non-allergenic rice protein isolate, potato protein isolates, canola protein isolate, pea protein isolate, and bovine serum albumin; each of which can be either native or denatured.

2.2. Any preceding Composition 2 et seq., wherein the protein particles comprise native or denatured whey protein isolate.

2.3. Any preceding Composition 2 et seq., wherein the protein is at least one protein chosen from of whey protein isolate, soy protein isolate, denatured whey protein isolate and denatured soy protein isolate.

2.4. Any preceding Composition 2 et seq., wherein the protein particles have an average diameter of from 500 nm to 20 μm.

2.5. Any preceding Composition 2 et seq., wherein the protein particles have a specific surface area of 3-16 $m^2/g$, for example 5-14 $m^2/g$, for example 7-12 $m^2/g$.

2.6. Any preceding Composition 2 et seq., wherein the protein particles have an internal surface area of 20-80 $m^2/g$, for example 30-70 $m^2/g$, for example 40-60 $m^2/g$.

2.7. Any preceding Composition 2 et seq., wherein the protein particles have a pore volume of 0.1-0.6 ml/g, for example 0.2-0.5 ml/g, for example 0.3-0.4 ml/g.

2.8. Any foregoing Composition 2 et seq., wherein the specific surface area of the particle is 3-16 $m^2/g$, the internal surface area of the particle is 20-80 $m^2/g$, and the pore volume of the particles is 0.1-0.6 ml/g.

2.9. Any foregoing Composition 2 et seq., wherein the specific surface area of the particle is 5-14 $m^2/g$, the internal surface area of the particle is 30-70 $m^2/g$, and the pore volume of the particles is 0.2-0.5 ml/g.

2.10. Any foregoing Composition 2 et seq., wherein the specific surface area of the particle is 7-12 $m^2/g$, the internal surface area of the particle is 40-60 $m^2/g$, and the pore volume of the particles is 0.3-0.4 ml/g.

2.11. Any preceding Composition 2 et seq., wherein at least two of said protein particles carry different fragrance agent of interest.

2.12. Any preceding Composition 2 et seq., wherein the protein particles are prepared by a method according to any of Methods 1 et seq. or 2 et seq.

Thus, the present disclosure also provides, in one embodiment, a method (Method 3) for imparting fragrance to a subject comprising applying to the subject a Composition according to any of Compositions 2 et seq.

The present disclosure also provides, in one embodiment, a method (Method 4) for preventing odor from a subject comprising applying to the subject a Composition according to any of Compositions 2 et seq.

The present disclosure also provides antiperspirant or deodorant compositions comprising protein particles prepared according to any of the foregoing methods, and the use of a porous protein particle prepared by any foregoing method in the manufacture of an antiperspirant or deodorant composition.

For antiperspirant and deodorant compositions of the disclosure, e.g., Composition 2, et seq., the carrier can be in the form of a stick, or an aerosol. For stick formulations, the carrier may include oils and/or silicones and gelling agents. An example of a formulation can be found in US2011/0076309A1, incorporated by reference herein.

Optional ingredients that can be included in an antiperspirant and/or deodorant composition of the disclosure include solvents; water-soluble alcohols such as $C_{2-8}$ alcohols including ethanol; glycols including propylene glycol, dipropylene glycol, tripropylene glycol and mixtures thereof; glycerides including mono-, di- and triglycerides; medium to long chain organic acids, alcohols and esters; surfactants including emulsifying and dispersing agents; amino acids including glycine; structurants including thickeners and gelling agents, for example polymers, silicates and silicon dioxide; emollients; fragrances; and colorants including dyes and pigments.

The compositions include topical antiperspirant and/or deodorant formulations suitable for application to skin, illustratively a stick, a gel, a cream, a soft solid, a powder, a liquid, an emulsion, a suspension, a dispersion or a spray. The composition can comprise a single phase or can be a multi-phase system, for example a system comprising a polar phase and an oil phase, optionally in the form of a stable emulsion. The composition can be liquid, semi-solid or solid. In some embodiments, the compositions are anhydrous. The antiperspirant and/or deodorant formulation can be provided in any suitable container such as an aerosol can, tube or container with a porous cap, bottle, container with an open end, etc.

Antiperspirant Active Materials

When the composition includes an antiperspirant active, any of the known antiperspirant active materials can be utilized in the composition. Antiperspirant actives include, but are not limited to, aluminum chlorhydrate, aluminum chloride, aluminum sesquichlorohydrate, aluminum-zirconium hydroxychlorides, complexes or adducts of the above-mentioned active ingredients with glycol, such as propylene glycol (for example, "Rehydrol" II from Reheis Chemical Co.), and combinations thereof. Known aluminum-zirconium salts in combination with neutral amino acids, such as glycine (e.g., aluminum-zirconium tetrachlorohydrex Gly) can also be used. Generally, any of the Category I active antiperspirant ingredients, listed in the Food and Drug Administration's Monograph on Antiperspirant Drug Products (the Monograph) for over-the-counter human use can be used.

In other embodiments, the antiperspirant active is an aluminum salt and/or an aluminum-zirconium salt, such as those described above, that are further stabilized by betaine and a calcium salt. More information about betaine and calcium salt stabilized antiperspirant salts can be found in U.S. Patent Application Publication No. 2006/0204463 to Tang et al., which is incorporated herein by reference only for the disclosure of the antiperspirant actives.

In other embodiments, the antiperspirant active, such as those described above, is selected to have a low metal to chloride ratio. Examples of these antiperspirant actives can be found in U.S. Pat. No. 6,375,937 to Chopra et al. and in U.S. Patent Application Publication No. 2004/0109833 to Tang et al., which are incorporated herein by reference only for their disclosure of the antiperspirant active.

In other embodiments, the type of salt of interest, an aluminum zirconium tetrasalt or octasalt free of glycine are used wherein aluminum zirconium salt is stabilized by Betaine and has a metal to chloride ratio of about 0.9:1 to about 1.3:1 (and in other embodiments of about 0.9:1 to about 1.2:1 or about 0.9:1 to about 1.1:1). For the tetrasalt, the Al/Zr atomic ratio can be about 3.2:1 to about 4.1:1.0 and the Betaine:zirconium mole ratio can be about 0.2:1 to about 3.0:1 (or in other embodiments of about 0.4:1 to about 1.5:1). Another salt that can be used is an aluminum chloride salt buffered by Betaine, wherein the salt has a metal to chloride ratio of 0.9:1 to 1.3:1 (and in other embodiments of about 0.9:1 to about 1.2:1 or about 0.9:1 to about 1.1:1). For the octasalt the Al/Zr atomic ratio is about 6.2:1 to about 10.0:1 and the Betaine:Zr mole ratio is about 0.2:1 to about 3.0:1 (or in other embodiments of about 0.4:1 to about 1.5:1). In one embodiment, in the case of a salt that contains zirconium, the Betaine is incorporated during the synthesis of the salt so as to maximize the stabilizing effect this ingredient has (especially on the zirconium species). Alternatively, it can be post added to a glycine-free salt along with additional active phase ingredients to form a Betaine stabilized active.

Examples of commercially available glycine-free low M:Cl ratio tetrasalts and octasalts include, but are not limited to, REZAL™ AZP 955 CPG and REZAL™ AZP 885 respectively (both from Reheis Chemical Company, Berkeley Heights, N.J.). A more detailed description of making such commercially available salts can be found for example, in U.S. Pat. Nos. 7,074,394 and 6,960,338. Further examples of making these types of salt complexes are described in U.S. Patent Application Publication No. 2004/0198998 and U.S. Pat. No. 7,105,691.

In addition to the anti-irritation properties of Betaine, it has also been found that antiperspirant formulations preserve their fragrance stability upon ageing when the Al/Zr salt is used in association with Betaine.

Additionally, the antiperspirant active can be a calcium salt stabilized antiperspirant active. Examples of calcium salt stabilized antiperspirant actives can be found in U.S. Patent Application Publication No. 2006/0204463, which is incorporated herein by reference only for the disclosure of the calcium salt stabilized antiperspirant actives.

In addition, any new ingredient, not listed in the Monograph, such as aluminum nitratohydrate and its combination with zirconyl hydroxychlorides and nitrates, or aluminum-stannous chlorohydrates, can be incorporated as an antiperspirant active. Antiperspirant actives can include, but are not limited to, the following: astringent salt of aluminum, astringent salt of zirconium, aluminum bromohydrate, aluminum chlorohydrate, aluminum dichlorohydrate, aluminum sesquichlorohydrate, aluminum chlorohydrex PG, aluminum dichlorohydrex PG, aluminum sesquichlorohydrex PG, aluminum chlorohydrex PEG, aluminum dichlorohydrex PEG, aluminum sesquichlorohydrex PEG, aluminum chloride, aluminum sulfate, aluminum zirconium chlorohydrate, aluminum zirconium trichlorohydrate, aluminum zirconium tetrachlorohydrate, aluminum zirconium pentachlorohydrate, aluminum zirconium octachlorohydrate, aluminum zirconium tetrachlorhydrex propylene glycol, aluminum zirconium trichlorhydrex Gly, aluminum zirconium tetrachlorohydrex Gly, aluminum zirconium pentachlorohydrex Gly, aluminum zirconium octachlorohydrex Gly, buffered aluminum sulfate, potassium alum, sodium aluminum chlorohydroxy lactate. In one embodiment, the antiperspirant active is aluminum chlorhydrate. In another embodiment, the antiperspirant active is aluminum zirconium tetrachlorhydrex propylene glycol.

Deodorant Active Materials

Any known deodorant active can be used. Examples of deodorant active include, but are not limited to, antimicrobial actives, alcohols, 2,4,4'-trichloro-2'-hydroxy diphenyl ether (Triclosan), benzethonium chloride, polyhexamethylene biguanides, triethylcitrate, 2-amino-2-methyl-1-propanol (AMP), cetyl-trimethylammonium bromide, cetyl pyridinium chloride, farnesol (3,7,11-trimethyl-2,6,10-dodecatrien-1-ol), bactericides, and/or bacteriostats.

The compositions can be used in a method to reduce sweating by applying the composition to skin. In certain embodiments, the application is to the axilla.

In another embodiment, the disclosure provides a soap, lotion or cleansing regimen product for personal care use, comprising Particles 1, et seq. together with water and surfactant, e.g., wherein the Particles contain a fragrance. In certain embodiments, the particles may contain a benefit agent to promote skin health, including, for example, skin barrier function repair or moisturization.

Home Care Products

In some embodiments, the present disclosure provides a laundry additive composition comprising (i) porous protein particle comprising a fragrance agent of interest loaded therein, and (ii) one of a water soluble carrier or a dryer sheet. In some embodiments, the water soluble carrier is at least one of an oxylated material and a salt. In some embodiments the disclosure provides methods for adding fragrance to laundry comprising adding a composition comprising a plurality of protein particles containing a fragrance to laundry. The composition can be added during a wash cycle, a rinse cycle or during drying. In some embodiments, the disclosure provides methods of making the laundry additive composition.

In a further embodiment the present disclosure provides a method (Method 5) for adding fragrance to laundry comprising adding a composition comprising a plurality of protein particles, e.g., according to Particle 1, et seq., containing a fragrance to laundry; for example:

5.1. Method 5, wherein the wherein the adding is during a wash cycle.
5.2. Method 5, wherein the wherein the adding is during a rinse cycle.
5.3. Method 5, wherein the wherein the adding is during drying.
5.4. Any preceding Method 5 et seq., wherein the porous protein particles are according to Particle 1, et seq., above.
5.5. Any preceding Method 5 et seq., wherein the porous protein particles are prepared by a method according to any of Methods 1 et seq. or 2 et seq. above.
5.6. Any preceding Method 5 et seq., wherein the composition further comprises at least one of a fabric conditioning active and a water soluble carrier.

5.7. Method 5.6, wherein the fabric conditioning active is at least one active chosen from a fabric softener and a silicone.

5.8. Method 5.6 or 5.7, wherein the water soluble carrier comprises an oxylated material, for example at least one of a nonionic oxylated material; an ionic oxylated material; or a nonionic or ionic oxylated material and a salt.

5.9. Method 5.8, wherein the oxylated material is at least one material chosen from polyoxyalkylene, a polyoxyalkylene fatty acid ester, and a polyoxyalkylene fatty alcohol ether.

5.10. Method 5.8 or 5.9, wherein the oxylated material is at least one of a polyethylene glycol; a polyalkylene polymer of formula:
H—$(C_2H_4O)_x$—$(CH(CH_3)CH_2O)_y$—$(C_2H_4O)_z$—OH;
wherein x is from 50 to 300; y is from 20 to 100, and z is from 10 to 200;
a polyethylene glycol fatty acid ester of formula: $(C_2H_4O)_q$—C(O)O—$(CH_2)_r$—$CH_3$; wherein q is from 20 to 200, and r is from 10 to 30;
a polyethylene glycol fatty alcohol ether of formula: HO—$(C_2H_4O)_s$—$(CH_2)_t$—$CH_3$; wherein s is from 30 to 250, and t is from 10 to 30;
polyethylene glycol methyl ester (avg. MW 3000-7000);
linear EO/PO polyglycol Methyl-Polyethylenglycol (MW: 8000-12000);
glyceryl ether EO-PO polymer (MW 15,000-20,000);
$C_{16-18}$ fatty alcohol polyoxyethylene ether;
polyethylene isodecyl ether (MW: 400); and
sodium fatty acid alcohol ether sulfate.

5.11. Any preceding Method 5.8-5.10, wherein the salt is at least one of sodium sulfate and sodium carbonate.

5.12. Any preceding Method 5.1 et seq., wherein the composition is anhydrous.

The disclosure also provides, in a further embodiment, a laundry additive Composition (Composition 3) comprising porous protein particles e.g., according to Particle 1, et seq., comprising a fragrance agent of interest loaded therein, and one of a water soluble carrier or a dryer sheet; for example:

3.1. Composition 3, wherein the water soluble carrier comprises an oxylated material, for example at least one of a nonionic oxylated material; an ionic oxylated material; or a nonionic or ionic oxylated material and a salt.

3.2. Composition 3.1, wherein the oxylated material is at least one material chosen from polyoxyalkylene, a polyoxyalkylene fatty acid ester, and a polyoxyalkylene fatty alcohol ether.

3.3. Composition 3.1 or 3.2, wherein the oxylated material is at least one of a polyethylene glycol;
a polyalkylene polymer of formula: H—$(C_2H_4O)_x$—$(CH(CH_3)CH_2O)_y$—$(C_2H_4O)_z$—OH;
wherein x is from 50 to 300; y is from 20 to 100, and z is from 10 to 200;
a polyethylene glycol fatty acid ester of formula: $(C_2H_4O)_q$—C(O)O—$(CH_2)_r$—$CH_3$; wherein q is from 20 to 200, and r is from 10 to 30;
a polyethylene glycol fatty alcohol ether of formula: HO—$(C_2H_4O)_s$—$(CH_2)_t$—$CH_3$; wherein s is from 30 to 250, and t is from 10 to 30;
polyethylene glycol methyl ester (avg. MW 3000-7000);
linear EO/PO polyglycol Methyl-Polyethylenglycol (MW: 8000-12000);
glyceryl ether EO-PO polymer (MW 15,000-20,000);
$C_{16-18}$ fatty alcohol polyoxyethylene ether;
polyethylene isodecyl ether (MW: 400); and
sodium fatty acid alcohol ether sulfate.

3.4. Any Composition 3.1-3.3, wherein the salt is at least one of sodium sulfate and sodium carbonate.

3.5. Any Composition 3-3.4, further comprising at least one fabric conditioning material chosen from a fabric softener and a silicone.

3.6. Any Composition 3, et seq., wherein the porous protein particles are according to Particle 1, et seq., above.

3.7. Any Composition 3 et seq., wherein the protein particles are prepared by a method according to any of Methods 1 et seq. or 2 et seq. above.

3.8. Any preceding Composition 3 et seq., wherein the composition is anhydrous.

The scent booster compositions of the disclosure are useful for imparting and/or enhancing fragrance delivery to clothes, preferably in a clothes washing machine.

The compositions of the disclosure are can be added in the wash cycle or a rinse cycle, although in preferred embodiments, the compositions of the disclosure are added in the wash cycle along with the detergent. In some embodiments, the compositions of the disclosure are a solid form, for example a tablet, powder or pastille, or dryer sheet, containing or composed of the fragrance-carrying protein particles described herein. The solid form disperses into, or releases, the porous protein particles either in the wash cycle, or in a rinse cycle, or slowly over both cycles.

The porous protein particles containing fragrance then release, or dissolve and release fragrance, which becomes associated with (i.e., bound to) the clothes. Preferably, the particles dissolve slowly over the course of the wash cycle, or both the wash cycle and the rinse cycle. While not wishing to be bound by a particular theory, it is believed that the particles act as a carrier for delivery of fragrance to the fabric. As the particles dissolve in proximity to the fabric, the less soluble fragrance deposits on the fabric. It is believed that slow dissolution of the particles affords more time for the released particles to adhere to the fabric being washed, resulting on more fragrance imparted to fabric upon dissolution of the particles.

Preferably, the solubility of the protein particles is such that release of fragrance is not so rapid as to allow the fragrance to be washed away by detergent, but not sufficiently slow to prevent full release of fragrance by completion of the rinse cycle. Thus, in some embodiments, the majority of the porous particles retains the loaded fragrance through the wash cycle, and release fragrance during the rinse cycle. In other embodiments, the majority of the porous particles releases the loaded fragrance in the wash cycle, and release the remaining fragrance during the rinse cycle.

Confectionary and Food Products Comprising the Particles

In a further embodiment, the disclosure provides confectionary products and food products comprising the particles, wherein the particles are loaded with flavoring agents and provide an enhanced or sustained release of flavor.

For example, the disclosure provides a chewing gum Composition (Composition 4) comprising a porous protein particle in a gum base, for example:

4.1. Composition 4, wherein the porous protein particle is a particle according to any of Particle 1 et seq. above, or is a particle prepared by any of the preceding Methods 1 et seq. or 2 et seq.

4.2. Composition 4 or 4.1, wherein the porous protein particle carries one or more flavorings, e.g., one or more flavoring oils and/or a sweetener.

4.3. Composition 4.2, comprising flavorings (e.g. sweeteners and/or flavoring oils) in the gum base addition to the porous protein particle, e.g., wherein the additional flavorings in the gum base provide an immediate taste when the gum is chewed and the flavor carried by the porous protein particles is released by chewing to provide a sustained taste.

4.4. Composition 4.2 or 4.3 wherein the flavorings are selected from one or more of non-saccharide sweeteners (e.g., one or more of aspartame, *stevia*, acesulfame K, sucralose and sugar alcohols, e.g., one or more of xylitol, sorbitol, maltitol, and mannitol), flavoring oils (e.g., one or more oils of spearmint, peppermint, wintergreen, *sassafras*, cinnamon, lemon, lime, grapefruit, and orange), cooling agents (e.g., menthol and/or methyl salicylate); and flavoring aldehydes, esters, and alcohols.

4.5. Any foregoing Composition 4, et seq. further comprising a softener, e.g., selected from one or more of glycerol, sugar alcohols, and vegetable oils.

4.6. Any foregoing Composition 4, et seq. further comprising a preservative.

4.7. Any foregoing Composition 4, et seq. wherein the specific surface area of the particles is 3-16 $m^2/g$, for example 5-14 $m^2/g$, for example 7-12 $m^2/g$.

4.8. Any foregoing Composition 4, et seq., wherein the internal surface area of the particles is 20-80 $m^2/g$, for example 30-70 $m^2/g$, for example 40-60 $m^2/g$.

4.9. Any foregoing Composition 4, et seq. wherein the pore volume of the particles is 0.1-0.6 ml/g, for example 0.2-0.5 ml/g, for example 0.3-0.4 ml/g.

4.10. Any foregoing Composition 4, et seq., wherein the specific surface area of the particle is 3-16 $m^2/g$, the internal surface area of the particle is 20-80 $m^2/g$, and the pore volume of the particles is 0.1-0.6 ml/g.

4.11. Any foregoing Composition 4, et seq., wherein the specific surface area of the particle is 5-14 $m^2/g$, the internal surface area of the particle is 30-70 $m^2/g$, and the pore volume of the particles is 0.2-0.5 ml/g.

4.12. Any foregoing Composition 4, et seq., wherein the specific surface area of the particle is 7-12 $m^2/g$, the internal surface area of the particle is 40-60 $m^2/g$, and the pore volume of the particles is 0.3-0.4 ml/g.

4.13. Any foregoing Composition 4, et seq. wherein the protein in the particle is native or denatured whey protein isolate.

It will be evident that in certain instances a single ingredient may serve more than one function. For example, in the chewing gum above, a sugar alcohol may function as a sweetener and/or as a softener, depending on the particular formulation.

In another embodiment, the disclosure provides a pet food product, for example a chew for a dog, comprising a particle according to any of Particle 1 et seq. above comprising a flavor, for example a palatability enhancer, and a chewable base, e.g., comprising rawhide, starch and/or polymer. According to one embodiment, the particle may include an agent for promoting canine or feline dental health or fresh breath. In a further embodiment, the particles may deliver vitamins or other pet health-related additives.

Oral Care Products

The particles of the present disclosure can also be utilized as carriers for components in oral care products, for example dentifrice compositions. The preparation of dentifrices compositions is well known in the art. U.S. Pat. Nos. 3,996,863, 3,980,767, 4,328,205 and 4,358,437, which are incorporated herein by reference, describe exemplary toothpastes and methods of production thereof. Dentifrice compositions often contain a flavoring agent, an antibacterial agent, or one or more of both. Flavoring agents are typically incorporated in dentifrice compositions at a concentration of about 0.1 to about 5% by weight.

Essential oils and herbal extracts are often included dentifrice compositions for both their flavor and antibacterial properties. Examples of essential oils suitable for inclusion in the presently disclosed protein particles include oils of spearmint, peppermint, wintergreen, *sassafras* clove, sage, *eucalyptus*, marjoram, cinnamon, lemon, lime, grapefruit, and orange, as well as rosemary extract, thymol, menthol, eucalyptol, and methyl salicylate. Other flavoring agents used in dentifrices include menthol, carvone, and anethole, and various flavoring aldehydes, esters, alcohols, and similar materials. Many these substances are hydrophobic in nature, and therefore especially amenable for incorporation into the particles disclosed herein.

Antimicrobial agents commonly used in dentifrice compositions suitable for inclusion in the presently disclosed porous protein particles include the essential oils described above, and halogenated diphenyl ether (triclosan), bisguanide antiseptics (e.g., chlorhexidine, alexidine, or octenidine), phenolic antiseptics, hexetidine, povidone iodine, delmopinol, salifluor, sanguinarine, propolis, cetyl pyridinium chloride, *magnolia* extract, magnolol, honokiol, butyl magnolol, propyl honokiol, and mixtures thereof.

Thus, in a further embodiment, the disclosure provides an Oral Care Composition (Composition 5) comprising a porous protein particle, for example:

5.1. Composition 5, wherein the porous protein particle is a particle according to any of Particle 1 et seq. above.

5.2. Composition 5 or 5.1, wherein the particles have loaded therein at least one agent of interest selected from flavoring agents, essential oils, herbal extracts and antimicrobial agents.

5.3. Any foregoing Composition 5 et seq., wherein the specific surface area of the particles is 3-16 $m^2/g$, for example 5-14 $m^2/g$, for example 7-12 $m^2/g$.

5.4. Any foregoing Composition 5 et seq., wherein the internal surface area of the particles is 20-80 $m^2/g$, for example 30-70 $m^2/g$, for example 40-60 $m^2/g$.

5.5. Any foregoing Composition 5 et seq., wherein the pore volume of the particles is 0.1-0.6 ml/g, for example 0.2-0.5 ml/g, for example 0.3-0.4 ml/g.

5.6. Any foregoing Composition 5 et seq., wherein the specific surface area of the particle is 3-16 $m^2/g$, the internal surface area of the particle is 20-80 $m^2/g$, and the pore volume of the particles is 0.1-0.6 ml/g.

5.7. Any foregoing Composition 5 et seq., wherein the specific surface area of the particle is 5-14 $m^2/g$, the internal surface area of the particle is 30-70 $m^2/g$, and the pore volume of the particles is 0.2-0.5 ml/g.

5.8. Any foregoing Composition 5 et seq., wherein the specific surface area of the particle is 7-12 $m^2/g$, the internal surface area of the particle is 40-60 $m^2/g$, and the pore volume of the particles is 0.3-0.4 ml/g.

5.9. Any foregoing Composition 5 et seq., wherein the protein is native or denatured whey protein isolate.

5.10. Any foregoing Composition 5 et seq., wherein the particles prepared by any of the preceding methods 1 et seq. or 2 et seq.

5.11. Any foregoing Composition 5 et seq., wherein the composition is a dentifrice.

5.12. Any foregoing Composition 5 et seq., wherein the composition is a toothpaste.

The following specific Examples are intended to illustrate particular embodiments of the disclosure.

Preparation of Protein Particles

Example 1—Heat Denaturation of Whey Protein Isolate

Whey protein isolate (WPI) is dissolved in MilliQ water to a final concentration of 10% by weight. The solution is heated in a water bath at 75° C. for 20 minutes (counted from reaching 74° C.), and then cooled in an ice water bath for at least 10 minutes, and the resulting dWPI solution is used the same day. The protein still possesses a net negative charge on the surface to enable further stabilization of particles.

Example 2—Preparation of 10% Methylcellulose Solution in Water

Methylcellulose powder is dispersed in hot water (95° C.) with vigorous stirring. The dispersion is placed in an ice bath with continued stirring. A clear solution forms upon cooling.

Example 3—Preparation of WPI-Stabilized Emulsion (Sample 1)

Batch size 200 ml; 15% solids. The dWPI solution is mixed with the 10% Methylcellulose solution, and a pre-emulsion is prepared by slowly adding the oil and additional water to the dWPI-10% methylcellulose solution while dispersing with an UltraTurrax disperser at maximum speed. The resulting pre-emulsion is passed through a microfluidizer at highest pressure (four passes) to produce the emulsion, which is used the same day.

Example 4—Preparation of Tween™ 80-Stabilized Emulsion (Samples 2 and 3)

Batch size 200 ml; 15% solids. The Tween™ 80 polysorbate is dissolved in water, and a pre-emulsion is prepared by slowing adding the oil to the Tween™ 80 solution. The resulting pre-emulsion is run through a microfluidizer at highest pressure (four passes) and mixed with the dWPI solution. The resulting emulsion (Sample 2) is used the same day. Sample 3 is prepared by adding 10% methylcellulose solution to the emulsion of Example 2.

Example 5—Preparation of Tween™ 80-Stabilized Emulsion (Sample 4)

Preparation is identical to Sample 2, except for the inclusion of 4% Tween™ 80 polysorbate.

Example 6—Preparation of Tween™ 80 and WPI-Stabilized Emulsion (Sample 5)

Batch size 200 ml; 15% solids. The WPI solution is mixed with Tween, and a pre-emulsion is prepared by slowing adding the oil and additional water to the WPI-Tween™ solution while dispersing with an UltraTurrax disperser at maximum speed. The resulting pre-emulsion is passed through a microfluidizer at highest pressure (four passes) to produce the emulsion, which is used the same day.

Example 7—Preparation of Lecithin-Stabilized Emulsion (Sample 6)

Batch size 200 ml; 15% solids. The lecithin is dissolved in oil, and a pre-emulsion is prepared by slowing adding the solution of lecithin in oil to water while dispersing with an UltraTurrax disperser at maximum speed. The resulting pre-emulsion is passed through a microfluidizer at highest pressure (four passes), and mixed with the WPI solution to produce the emulsion, which is used the same day.

Example 8—Preparation of dWPI-Oil Emulsion without Methylcellulose or Surfactant (Sample 7)

A pre-emulsion is prepared by slowing adding the oil to the dWPI solution while dispersing with an UltraTurrax disperser at maximum speed. The resulting pre-emulsion is passed through a microfluidizer at highest pressure (four passes) to produce the emulsion, which is used the same day.

Example 9—Preparation of Native WPI-Oil Emulsion without Methylcellulose or Surfactant (Sample 8)

Sample 8 is prepared according to the same procedure as Example 7, except for use of native WPI.

The different formulations and procedures are summarized in Tables 1-3 below.

TABLE 1

Summary of formulations and procedures

| Sample | Surfactant | Addition of WPI or dWPI | Addition of MeC | Extraction Solvent |
|---|---|---|---|---|
| 1 | WPI | Before oil | To emulsion | Acetone or $SCCO_2$ |
| 2 | Tween ™ 80 polysorbate (2%) | After emulsification | — | Acetone or $SCCO_2$ |
| 3 | Tween ™ 80 polysorbate (2%) | After emulsification | To emulsion | Acetone or $SCCO_2$ |
| 4 | Tween ™ 80 polysorbate (4%) | After emulsification | — | Acetone or $SCCO_2$ |
| 5 | WPI + Tween ™ 80 polysorbate | Before oil, mixed with Tween ™ 80 | — | Acetone or $SCCO_2$ |
| 6 | Lecithin (in oil) | After emulsification | — | Acetone or $SCCO_2$ |
| 7 | None | With oil before emulsification | N/A | $SCCO_2$ |
| 8 | None | With oil before emulsification | N/A | $SCCO_2$ |

Tables 2 and 3 show the compositions of the solids and emulsions for the eight formulations of Table 1.

TABLE 2

| | Composition of solids | | | | Composition of emulsion | | | |
|---|---|---|---|---|---|---|---|---|
| sample | rapeseed oil (%) | WPI (%) | Tween ™ 80 polysorbate (%) | MeC (%) | rapeseed oil (g) | WPI solution (g) | Tween ™ 80 polysorbate (g) | MeC solution (g) |
| 1 | 60 | 35 | 0 | 5 | 18 | 105 | 0 | 15 |
| 2 | 60 | 38 | 2 | 0 | 18 | 114 | 0.6 | 0 |
| 3 | 60 | 33 | 2 | 5 | 18 | 99 | 0.6 | 15 |

TABLE 3

| | | Composition of solids | | | Composition of emulsion | | | |
|---|---|---|---|---|---|---|---|---|
| sample | surfactant | rapeseed oil (%) | WPI** (%) | surfactant (%) | rapeseed oil (g) | WPI solution (g) | surfactant (g) | Water (g) |
| 4 | Tween ™ 80 polysorbate | 60 | 36 | 4 | 18 | 108 | 1.2 | 72.8 |
| 5 | Tween ™ 80 polysorbate + WPI | 60 | 36 | 4 | 18 | 108 | 1.2 | 72.8 |
| 6 | lecithin | 60 | 36 | 4 | 18 | 108 | 1.2 | 72.8 |
| 7 | None | 60 | 40 | N/A | 72 | 480 | N/A | 248 |
| 8 | None | 57 | 38** | N/A | 72 | 480 | N/A | 248 |

**Samples 1-7 contained denatured WPI; Sample 8 contained native WPI

Example 10—Spray Drying

The emulsions are spray dried in a laboratory spray dryer having a drying column that is 0.75 m in length and 0.15 m in diameter. The spray dryer operates co-currently and has two fluid spray-nozzles with an orifice of 1.5 mm in diameter. The inlet and outlet temperature is kept at 180° C. and 70° C., respectively. The atomization airflow and feed flow is kept constant at 28 l/min and 5 ml/min, respectively. The particles flow into a cyclone and are collected in an Erlenmeyer flask.

Example 11—Oil Extraction

Extraction with Solvent:

The efficiency of microencapsulation (loading) is measured gravimetrically by adding one gram of powder to 6 ml solvent (acetone or petroleum ether) and shaking for two minutes. The solvent residue is then separated by filtration and the solid residue is washed with four Pasteur pipettes of the solvent. The vessels with solvent are placed in a 70° C. water bath until most solvent have evaporated. Then, the vessels are placed in a 105° C. oven until a constant weight is obtained. The powder is air-dried on the filter paper, collected and weighed.

Extraction with Supercritical Carbon Dioxide ($SCCO_2$):

Samples consisting of a few grams of powder are extracted with supercritical carbon dioxide at 350 bar, 45° C. for 1 hour. The oil is continuously removed. Extraction efficiency for $SCCO_2$ extracted particles is measured gravimetrically, before and after extraction.

Extraction efficiency for $SCCO_2$-extracted samples 7 and 8 is greater than 98%. In general, extraction efficiencies for solvent extracted particles are lower than for $SCCO_2$-extracted particles. For example, acetone extracted particles having compositions (dWPI/MCT Oil/MeC)=40/60/0, 35/60/5 and 30/60/10, respectively, have an extraction deficiency of 53%, 41% and 45%, respectively, where as the extraction efficiencies for the same particles extracted with $SCCO_2$ are 102%, 96% and 93%, respectively. (Note that measured extraction values in excess of 100% reflect range of experimental error).

Example 12—Scanning Electron Micrography (SEM) of Prepared Particles

Samples are mounted on double-sided adhesive tape attached to SEM tubes. The samples are covered with gold by sputtering the samples for 180 seconds, with use of a sputter coater (Balzers, Switzerland). Subsequently the samples are examined with an ESEM instrument operated at 15-30 keV in high vacuum mode.

The SEM images showed that the particle structure is influenced by the order of addition of surfactants, in particular which surfactant that is used to generate the primary emulsion. When WPI is added to an emulsion prepared with Tween™ 80 polysorbate or lecithin, it appears that this small molecule surfactant is not displaced by the protein.

The addition of Tween™ 80 polysorbate causes the particles to become more spherical, and pores on the surface are generated. Similar pores are found on the particles with lecithin, but these particles are not spherical. These larger surface pores are not observed in Samples 1, 3 or 5, described in Table 4 below.

The internal structure of the particles is observed by chopping the particles with a razor blade prior to imaging in SEM. All samples showed porous walls, with larger pores towards the central vacuole compared to the external surface. The central vacuole is present in a large fraction of the particles, in particular the spherical particles.

In general, the surface of particles prepared using native WPI is more porous, especially when acetone is used as extraction solvent, and the particles are readily soluble in water. Such particles thus may be particularly advantageous if instant or relatively rapid release of the carried active is desired. When heat-denatured WPI is used as the matrix material, the particles are slightly less porous, the surface contains much fewer pores, and the particles are insoluble in water. Thus, these particles may be particularly advantageous in applications where intermediate-extended release is desired. Significantly, the dWPI derived particles still interact with water and become gel-like when exposed to water for extended periods of time.

The dWPI particles can be further modified by adjusting the pH of the solution to the isoelectric point of the protein to render the surface charge zero and retain the hydrophobic actives for a longer time. pH of the solution can be also be manipulated to optimize the release of the actives.

Table 4 below describes particle and pore morphology for some formulations shown in Table 1.

TABLE 4

| Sample | Surfactant | Addition of WPI or dWPI | Addition of MeC | Extraction Solvent | Type of particles and pores |
|---|---|---|---|---|---|
| 1 | WPI | Before oil | To emulsion | Acetone or $SCCO_2$ | |
| 2 | polysorbate 80 (Tween ™ 80) (2%) | (WPI) After emulsification | — | Acetone or $SCCO_2$ | Spherical, large surface pores |
| 2a | polysorbate 80 (Tween ™ 80) (2%) | (WPI) After emulsification | — | Acetone | Spherical, large surface pores, more pores, readily soluble in water, rapid release of actives |
| 2b | polysorbate 80 (Tween ™ 80) (2%) | (dWPI) After emulsification | — | Acetone | Spherical, large surface pores, less pores, insoluble particles, gel like in water, extended release of actives |
| 3 | polysorbate 80 (Tween ™ 80) (2%) | After emulsification | To emulsion | Acetone or $SCCO_2$ | |
| 4 | polysorbate 80 (Tween ™ 80) (4%) | After emulsification | — | Acetone or $SCCO_2$ | Spherical, large surface pores (releases hexyl benzoate or medium polarity solvents slowly) |
| 5 | WPI + polysorbate 80 (Tween ™ 80) | Before oil, mixed with Tween ™ 80 | — | Acetone or $SCCO_2$ | |
| 6 | Lecithin (in oil) | After emulsification | — | Acetone or $SCCO_2$ | Non-spherical particles with large pores |
| 7 | None | With oil before emulsification | N/A | $SCCO_2$ | |
| 8 | None | With oil before emulsification | N/A | $SCCO_2$ | |

The best extraction efficiency by organic solvent is obtained with methyl cellulose as additive and acetone as solvent. It is surprising that a modified cellulose enables significantly better extraction of the oil when using an organic solvent, increasing the extraction efficiency from about 3-5% to 60% and greater. Use of $SCCO_2$ as the extraction solvent results in much higher extraction efficiency—up to 100% removal of the template is obtained. Accordingly, the use of $SCCO_2$ as extraction medium is particularly attractive for powders intended for use in applications concerning actives that are released near or in the body, for example foods, pharmaceutics, etc., and for the scent booster and antiperspirant and/or deodorant embodiments of the disclosure.

The porosity of the particles is measured by Brunauer-Emmett-Teller (BET) analysis. The specific surface are of the extracted particles is 9.2 $m^2/g$, and the internal surface area of the extracted particles is about 50 $m^2/g$. The pore volume is about 0.3-0.4 ml/g.

Example 13—Light Microscopy of Prepared Particles

The behavior of the particles in water is investigated with light microscopy, where water is added to the dry powder and the events are observed in real time. The penetration of water into the particles is observed to be immediate. The particles prepared with denatured WPI do not dissolve, but swell to some extent, whereas the particles prepared with native WPI dissolve in water. Accordingly, particles prepared with denatured WPI are particularly useful in aqueous formulations and to provide extended release of carried actives.

Example 14—Release Experiments

Loading of Actives into $SCCO_2$-Extracted Particles:

A portion of extracted powder is placed in a small vial, and the active substance hexyl benzoate (Log P=4.85, solubility in water=0.0089 g/l), N-ethylpyrrolidone (NEP) (Log P=−0.2 at 23° C., solubility in water=1000 g/l at 20° C.) or α-tocopherol Log P=9.9, solubility in water=0.0000209 g/l) added drop wise while stirring intensely with a spatula. The added weight of active is carefully recorded. Addition of active is stopped either when the powder just began to become cohesive, or when a pre-specified amount of active have been added. The loading levels for hexyl benzoate, M-ethylpyrrolidone and α-tocopherol are 25-28%, based on gravimetric analysis. Presence of the agent of interest inside the particles is confirmed by confocal Raman microscopy.

Release of Hexyl Benzoate from $SCCO_2$-Extracted Particles into 1% SDS:

Release of hexyl benzoate, NEP and α-tocopherol are monitored for a period of 3-24 hours, in glass bottles (250 ml) placed on a slowly rocking table at 30° C. The powder is placed into the solution (1% SDS in MilliQ water for hexyl benzoate and NEP; 2.8% SDS in MilliQ water for α-tocopherol). Samples are withdrawn periodically and analyzed spectrophotometrically, or continuously monitored by pumping sample through the spectrophotometer flow cell. In the latter case, the tubing leading to the flow cell is fitted with a filter, which is replaced if it became clogged.

Results:

The release of hexyl benzoate from the porous protein particles is rapid and complete. The release rate is similar in each of the protein particle samples shown in Table 1, with the exception of sample 4, which showed a slightly lower rate of release. Particles loaded with water soluble N-ethylpyrrolidone or hydrophobic α-tocopherol, are released into water and 2.8% SDS, respectively. The release of NEP is rapid (approximately 90% released within 100 minutes). While not wishing to be bound by a particular theory, it is believed that this indicates that the pores in the protein particles are very hydrophobic and are very effective for entrapping both hydrophilic and hydrophobic actives, while holding extending the release of hydrophobic actives very significantly over hydrophilic actives. The release rate may also be limited by the solvation capacity of the release medium for a hydrophobic active. The release rate for α-tocopherol for solvent (acetone) extracted particles is slower, showing only 70-75% release after three hours. The release rate for α-tocopherol for $SCCO_2$ extracted particles is also slower, but is close to complete release after three hours. Acetone extracted particles have a different morphology and pore distribution than the $SCCO_2$ extracted particles, with acetone extracted particles possibly being favored for long term release.

Example 15—Antiperspirant Sticks Containing Particles Loaded with Fragrance

Antiperspirant (AP) sticks are prepared incorporating particles loaded with fragrance. Particles prepared according to the procedures of samples 7 and 8, above are loaded with liquid fragrance by slowly adding liquid fragrance to an equal weight of particles while mixing the powder (50% load). The compositions of the samples are shown below in Table 5.

TABLE 5

| Ingredient | Weight %-Control (A) | Weight % B | Weight % C |
| --- | --- | --- | --- |
| Palm Kernel Oil | 27 | 27 | 27 |
| C12-15 Alkyl Benzoate | 17 | 17 | 17 |
| Aluminum Zirconium Tetrachlorohydrex Gly | 22 | 22 | 22 |
| Cyclomethicone | 13 | 13 | 13 |
| Paraffin | 11 | 11 | 11 |
| PEG-8 Distearate | 4 | 4 | 4 |
| Hydrogenated Soybean Oil | 4 | 4 | 4 |
| Fragrance Loaded Sample (50% Fragrance Loading) | 1 (Starch Encap) | 1 (WPI 7) | 1 (WPI 8) |
| Fragrance & Minors | QS to 100 | QS to 100 | QS to 100 |

The particles are collected and dried and incorporated into an AP formulation at concentration of 1% by weight of the formulation. The time the fragrance lasted is evaluated against a control with traditional starch encapsulated fragrance (containing the same 50% concentration of the same fragrance) by three sensory evaluation experts. Particles prepared with native WPI (C) are parity to the control-A (i.e., no better retention of fragrance intensity after 4, 8, 12 and 22 hours), while the particles prepared with denatured WPI (B) showed increased retention of fragrance intensity after 4, 8 and 12 hours. Thus, the protein particles are advantageously employed as carriers for fragrance materials, for example for products, such as, for example antiperspirant sticks, roll-ons, and aerosols. Traditional starch based AP products have also a tendency to yellow with time upon aging at 40° C. AP stick based on WPI particles did not yellow upon aging at 40° C. for 3 months, thus demonstrating an additional advantage of WPI particles for these compositions.

Example 16—Preparation of Scent Booster Composition Containing Particles Loaded with Fragrance Scent booster compositions are prepared incorporating whey protein particles loaded with fragrance as prepared above.

The deposition of fragrance on garments is measured by sensory evaluation by a panel of twenty individuals for a scent booster composition of the disclosure (Composition A) versus two commercially available solid form scent boosters (Compositions B and C). The garments required for the evaluation are prepared by washing with un-fragranced detergent and with the solid forms. The washed garments then are tumble dried at 60° C. for 45 minutes.

The sensory panel evaluated the towels under damp conditions as well as under dry conditions, both pre- and post-rub, for both fragrance intensity and overall liking. Results showed that for wet towels the delivery of fragrance as measured by perceived intensity and liking of the composition of the disclosure is comparable to the commercial products. Similarly, results obtained for dry towels also clearly suggest delivery of fragrance through intensity and liking under dry conditions is comparable to the commercial products.

The results indicate that the whey protein particles described herein are able to load and deliver fragrance in a scent boosting composition in a manner comparable to commercial formulations. While not wishing to be bound by a particular theory, it is believed that this unexpected behavior is attributable primarily to the whey protein. Thus, the protein particles are advantageously employed as carriers for fragrance materials for scent boosting compositions.

Example 17—Preparation of Additional Scent Booster Composition

A scent booster composition is prepared incorporating whey protein particles loaded that are not pre-loaded with fragrance, as shown below in Table 6:

TABLE 6

| Formulation A | % W/W |
| --- | --- |
| Polypropylene Glycol Polyoxyalkylene | 31.5 |
| Polyethylene Glycol 1450 USP/NF | 31 |

TABLE 6-continued

| Formulation A | % W/W |
|---|---|
| Free Fragrance | 4.5 |
| Glycerin | 5 |
| Clay | 25 |
| Whey protein particles | 3 |
| | 100 |

The whey protein particles are added to the formulation containing free fragrance. The formulations are evaluated against identical formulations lacking whey protein particles, and again an identical formulation also containing a source of encapsulated fragrance.

Example 18—Preparation of Dentifrice Compositions Containing Particles Loaded with Flavor or Antibacterial Agent Two dentifrice formulas are prepared according to Example 2 of U.S. App. Pub. No. 20130129643, incorporated by reference in its entirety, having the magnolol and flavor and components respectively placed with porous particles of the disclosure as shown below in Table 7:

TABLE 7

| Ingredient (%) | Formula 1 | Formula 2 |
|---|---|---|
| Sodium CMC | 0.65 | 0.65 |
| Na Saccharine | 0.27 | 0.27 |
| Water (DI) | Q.S. | Q.S. |
| Sodium fluoride | 0.243 | 0.243 |
| Titanium Dioxide | 0.75 | 0.75 |
| Sorbitol | 54 | 54 |
| PEG 600 | 3 | 3 |
| Silica High Cleaning | 10 | 10 |
| Silica Thickener | 2.75 | 2.75 |
| Silica Abrasive | 10 | 10 |
| Flavor (spearmint) | 1.15 | 0 |
| Particles with Flavor (spearmint) | 0 | 1.15 |
| Particles with Magnolol | 0.5 | 0 |
| Magnolol | 0 | 0.5 |
| Sodium Lauryl Sulfate | 1.5 | 1.5 |
| Cocoamidopropyl Betaine | 1.25 | 1.25 |
| Zinc Oxide Powder | 0.5 | 0.5 |
| Total | 100 | 100 |

Formulae 1 and 2 contain particles of the disclosure prepared as shown in the Examples above for Sample 7 in Table 1. The particles in Formula 1 are loaded with magnolol (loading to 50%) using the procedure of Example 14. The particles in Formula 2 are loaded with spearmint (loading to 50%) as flavor, also using the procedure of Example 14.

The dentifrices of Formulas 1 and 2 each are expected to display excellent antibacterial and flavor characteristics.

Example 19—Preparation of Chewing Gum Containing Particles Loaded with Sweetener High intensity sweeteners as well as flavors are commonly known and used in chewing gum formulations. The rapid release of the flavor can result in a taste profile that can be described as a rapid burst of sweetness. Usually, high intensity sweeteners such as aspartame, reach their peak sweet taste rapidly, with the intensity of sweet taste rapidly declining soon thereafter. The initial rapid burst can be unpleasant to many consumers as the strong sweet taste tends to overpower the other flavors that may be present in the gum composition. The relatively rapid loss of sweetness can also result in a bitter aftertaste. Accordingly, there have been attempts to encapsulate high intensity sweeteners in gum compositions.

In one embodiment, particles of the present disclosure loaded with flavor compounds can be incorporated into chewing gum compositions to afford slower release of flavor components.

A chewing gum is prepared having the following composition:
Gum base: 20-40%
Polyols and bulking agents (sugar): 10-50%
Flavoring compound: 0.01-10%
Particles of the disclosure as described for Example 18, loaded with high intensity sweeteners: 0.01-10%
Non-hydrated hydrocolloid (including encapsulated): 1.5%-20% (or 2-5%)

The chewing gum is prepared by compounding the gum base and then adding the flavors, sweeteners and hydrocolloid. The resulting chewing gum is provides an initial flavor due to the free flavoring in the composition, but then continues to release sweetener from the particles of the disclosure, providing a more pleasant taste experience.

Example 20—Preparation of Chewing Gum Containing Particles Loaded with Flavor

Chewing Gum compositions are prepared as in Example 19, also containing particles of the disclosure as described in Example 18 herein, loaded with flavor compound. The resulting gum is expected to have excellent flavor characteristics.

Preparation of Baked Goods Containing Particles Loaded with Active

Example 21—Preparation of Biscuit Containing Particles Loaded with Flavor Active The conventional ingredients for a biscuit, including flour, shortening, leavening, water, sugar, and flavorants, including from about 0.1% to about 10% of the protein particles as described for Example 18, loaded with flavorant, are mixed together and formed by known techniques. The biscuits are then baked under standard processing conditions to produce a final biscuit product. For example, in one embodiment, 2 cups all-purpose flour, 1 tablespoon baking powder, 2 tablespoons of the protein particles as described for Example 19, loaded with flavorant and ½ teaspoon salt are sifted together. ½ cup shortening is cut in and the mixture is blended until mixture resembles coarse crumbs. ¾ cup of milk is poured into the flour mixture while stirring, and is mixed in until the dough is soft, moist and pulls away from the side of the container. The dough is turned out onto a lightly floured surface and tossed with flour until no longer sticky. The dough is then rolled out into a ½ inch thick sheet and cut to size. The biscuits are baked on ungreased baking sheets until golden brown.

Example 22—Preparation of Cake Containing Particles Loaded with Flavor Active 1 cup (2 sticks) unsalted butter and 1¾ cups of sugar are mixed with an electric mixer until light and fluffy, about 6 minutes. 4 eggs plus 2 yolks are beat in, one at a time, until combined. 1 tablespoon of pure vanilla extract is then beat in. 3 cups cake flour (spooned and leveled), 1 tablespoon baking powder and ½ teaspoon fine salt are whisked together and one third of this mixture is added with mixing, to the butter mixture, to combine. To this mixture is added, with mixing, ¾ cup buttermilk, another ⅓ the flour mixture, another ¾ cup buttermilk, 2 tablespoons of the protein particles as described for Example 18, loaded with flavorant, and the remaining flour mixture until just combined. The mixture is baked at 350° F. for 10-12 minutes.

What is claimed is:

1. A porous protein particle prepared by a method comprising:
   providing a protein isolate;
   forming a protein isolate emulsion with an oil;
   drying the protein isolate emulsion to produce a powder; and
   extracting the oil from the powder to produce the porous protein particle;
   wherein the protein particle has an average diameter of from 500 nm to 20 µm; and has one or more characteristics selected from: a specific surface area of 3-16 $m^2/g$, or 5-14 $m^2/g$, or 7-12 $m^2/g$; an internal surface area of 20-80 $m^2/g$, or 30-70 $m^2/g$, or 40-60 $m^2/g$; and a pore volume of 0.1-0.6 ml/g, or 0.2-0.5 ml/g, or 0.3-0.4 ml/g;
   wherein the protein isolate is whey protein isolate, which can be either native or denatured; and
   wherein the protein particle further comprises a flavor or a fragrance.

2. A composition comprising a plurality of porous protein particles according to claim 1.

3. A composition of claim 2, wherein said composition is an antiperspirant or deodorant composition comprising (i) at least one of an antiperspirant active, a deodorant active, and free fragrance, and (ii) a plurality of protein particles containing a fragrance.

4. The composition of claim 2 wherein the composition is:
   a soap for personal care; wherein the porous protein particles comprise a fragrance and/or antibacterial agent loaded therein; or
   a laundry additive composition, wherein the porous protein particles comprise a fragrance loaded therein; and the laundry additive composition optionally further comprises one of a water soluble carrier or a dryer sheet.

5. The composition of claim 4 further comprising at least one fabric conditioning material chosen from a fabric softener and a silicone.

6. A method for adding fragrance to laundry comprising adding a composition according to claim 4 to laundry.

7. The composition of claim 2, wherein the composition is a dentifrice, a toothpaste or a chewing gum.

8. The composition of claim 2 wherein at least two of said protein particles carry different agents of interest.

9. A food substance, confectionary, beverage, pharmaceutical, biocide, pesticide, personal care product, oral care product or laundry product comprising a porous protein particle according to claim 1.

10. The particle of claim 1, wherein the protein isolate emulsion is formed by a procedure comprising one of:
    a. emulsifying an oil with one or more surfactants with an HLB of 8 to 18;
    b. emulsifying an oil with a surfactant having an HLB of 14 to 18 in the water phase and surfactant with an HLB of 1 to 6 in the oil phase; or
    c. mixing a surfactant stabilized emulsion with the protein isolate.

11. The particle of claim 1, wherein the forming of the protein isolate emulsion comprises any of procedures (a)-(e):
    (a) i) providing a mixture comprising an oil, a surfactant and water;
        ii) homogenizing or fluidizing the mixture to form a surfactant stabilized emulsion;
        iii) combining the protein isolate and the surfactant stabilized emulsion to form a protein isolate-surfactant stabilized emulsion; and
        iv) optionally combining the protein isolate-surfactant stabilized emulsion with a further component;
    (b) i) providing a mixture comprising the protein isolate, a modified cellulose, and water; and
        ii) combining the mixture with an oil to form an emulsion; and
        iii) homogenizing or fluidizing the emulsion;
    (c) i) providing a mixture comprising the protein isolate and a surfactant; and
        ii) combining the mixture with an oil to form an emulsion; and
        iii) homogenizing or fluidizing the emulsion;
    (d) i) providing a mixture comprising an oil, an amphipathic surfactant, and water to form an emulsion;
        ii) homogenizing or fluidizing the emulsion; and
        iii) combining the protein isolate and the emulsion;
    (e) i) combining an oil with the protein isolate together with water; and
        ii) homogenizing or fluidizing the mixture to form an emulsion.

12. The particle of claim 1, wherein the protein isolate is dissolved or suspended in water.

13. The particle of claim 1, wherein the oil is selected from rapeseed oil, soybean oil, triglyceride oils and medium-chain triglyceride oil.

14. The particle of claim 11, wherein the modified cellulose comprises one or more of hydroxypropyl methyl cellulose, methyl cellulose, and hydroxypropyl cellulose.

15. The particle of claim 1, wherein the extracting of the powder comprises extracting with supercritical carbon dioxide or extracting with an organic solvent.

16. The particle of claim 1, wherein the emulsion is homogenized to produce an average droplet diameter of from 100 nm to 1000 nm; or 100 nm to 300 nm, or about 200 nm.

* * * * *